(12) United States Patent
Tang et al.

(10) Patent No.: US 8,846,070 B2
(45) Date of Patent: *Sep. 30, 2014

(54) BIOLOGICALLY DEGRADABLE COMPOSITIONS FOR MEDICAL APPLICATIONS

(75) Inventors: Yiwen Tang, San Jose, CA (US); Syed F. A. Hossainy, Fremont, CA (US); Andrew C. Tung, Santa Clara, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 756 days.

This patent is subject to a terminal disclaimer.

(21) Appl. No.: 12/182,066

(22) Filed: Jul. 29, 2008

(65) Prior Publication Data

US 2008/0279898 A1 Nov. 13, 2008

Related U.S. Application Data

(63) Continuation of application No. 10/812,780, filed on Mar. 29, 2004, now abandoned.

(51) Int. Cl.
| | | |
|---|---|---|
| *A61K 9/00* | (2006.01) | |
| *A61F 2/00* | (2006.01) | |
| *A61K 47/30* | (2006.01) | |
| *A61L 31/10* | (2006.01) | |
| *A61L 27/34* | (2006.01) | |

(52) U.S. Cl.
CPC ........ *A61L 27/34* (2013.01); *A61L 31/10* (2013.01)
USPC ........... 424/423; 424/400; 424/425; 424/426; 514/772.3

(58) Field of Classification Search
USPC ............... 424/423, 425, 426, 400; 514/772.3
See application file for complete search history.

(56) References Cited

U.S. PATENT DOCUMENTS

| | | | |
|---|---|---|---|
| 3,839,743 A | 10/1974 | Schwarcz | |
| 3,900,632 A | 8/1975 | Robinson | |
| 4,110,497 A | 8/1978 | Hoel | |
| 4,321,711 A | 3/1982 | Mano | |
| 4,346,028 A | 8/1982 | Griffith | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,768,507 A | 9/1988 | Fischell et al. | |
| 4,776,337 A | 10/1988 | Palmaz | |
| 4,816,339 A | 3/1989 | Tu et al. | |
| 4,850,999 A | 7/1989 | Planck | |
| 4,877,030 A | 10/1989 | Beck et al. | |
| 4,878,906 A | 11/1989 | Lindemann et al. | |
| 4,879,135 A | 11/1989 | Greco et al. | |
| 4,902,289 A | 2/1990 | Yannas | |
| 4,977,901 A | 12/1990 | Ofstead | |
| 4,994,298 A | 2/1991 | Yasuda | |
| 5,019,090 A | 5/1991 | Pinchuk | |
| 5,028,597 A | 7/1991 | Kodama et al. | |
| 5,059,211 A | 10/1991 | Stack et al. | |
| 5,062,829 A | 11/1991 | Pryor et al. | |
| 5,084,065 A | 1/1992 | Weldon et al. | |
| 5,085,629 A | 2/1992 | Goldberg et al. | |
| 5,100,429 A | 3/1992 | Sinofsky et al. | |
| 5,108,755 A | 4/1992 | Daniels et al. | |
| 5,112,457 A | 5/1992 | Marchant | |
| 5,123,917 A | 6/1992 | Lee | |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,167,614 A | 12/1992 | Tessmann et al. | |
| 5,192,311 A | 3/1993 | King et al. | |
| 5,197,977 A | 3/1993 | Hoffman, Jr. et al. | |
| 5,234,456 A | 8/1993 | Silvestrini | |
| 5,234,457 A | 8/1993 | Andersen | |
| 5,236,447 A | 8/1993 | Kubo et al. | |
| 5,279,594 A | 1/1994 | Jackson | |
| 5,282,860 A | 2/1994 | Matsuno et al. | |
| 5,289,831 A | 3/1994 | Bosley | |

(Continued)

FOREIGN PATENT DOCUMENTS

| | | |
|---|---|---|
| DE | 44 07 079 | 9/1994 |
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |

(Continued)

OTHER PUBLICATIONS

International Search Report for PCT/US2005/009881 filed Mar. 24, 2005, mailed Sep. 23, 2005, 13 pgs.

(Continued)

*Primary Examiner* — Abigail Fisher

(74) *Attorney, Agent, or Firm* — Squire Patton Boggs (US) LLP

(57) ABSTRACT

A medical article is disclosed, comprising a biologically degradable AB block copolymer and a biologically degradable polymer that is capable, at equilibrium and at room temperature, of absorbing less than about 5 mass % water.

17 Claims, No Drawings

(56) References Cited

U.S. PATENT DOCUMENTS

| | | | |
|---|---|---|---|
| 5,290,271 A | 3/1994 | Jernberg | |
| 5,306,286 A | 4/1994 | Stack et al. | |
| 5,306,294 A | 4/1994 | Winston et al. | |
| 5,328,471 A | 7/1994 | Slepian | |
| 5,330,500 A | 7/1994 | Song | |
| 5,342,348 A | 8/1994 | Kaplan | |
| 5,342,395 A | 8/1994 | Jarrett et al. | |
| 5,342,621 A | 8/1994 | Eury | |
| 5,356,433 A | 10/1994 | Rowland et al. | |
| 5,383,925 A | 1/1995 | Schmitt | |
| 5,385,580 A | 1/1995 | Schmitt | |
| 5,389,106 A | 2/1995 | Tower | |
| 5,441,515 A | 8/1995 | Khosravi et al. | |
| 5,443,458 A | 8/1995 | Eury | |
| 5,455,040 A | 10/1995 | Marchant | |
| 5,464,650 A | 11/1995 | Berg et al. | |
| 5,474,563 A * | 12/1995 | Myler et al. | 606/108 |
| 5,502,158 A | 3/1996 | Sinclair et al. | |
| 5,508,036 A * | 4/1996 | Bakker et al. | 424/424 |
| 5,514,379 A | 5/1996 | Weissleder et al. | |
| 5,527,337 A | 6/1996 | Stack et al. | |
| 5,554,120 A | 9/1996 | Chen et al. | |
| 5,556,413 A | 9/1996 | Lam | |
| 5,578,046 A | 11/1996 | Liu et al. | |
| 5,578,073 A | 11/1996 | Haimovich et al. | |
| 5,591,607 A | 1/1997 | Gryaznov et al. | |
| 5,593,403 A | 1/1997 | Buscemi | |
| 5,593,434 A | 1/1997 | Williams | |
| 5,599,301 A | 2/1997 | Jacobs et al. | |
| 5,599,922 A | 2/1997 | Gryaznov et al. | |
| 5,605,696 A | 2/1997 | Eury et al. | |
| 5,629,077 A | 5/1997 | Turnlund et al. | |
| 5,631,135 A | 5/1997 | Gryaznov et al. | |
| 5,637,113 A | 6/1997 | Tartaglia et al. | |
| 5,667,767 A | 9/1997 | Greff et al. | |
| 5,670,558 A | 9/1997 | Onishi et al. | |
| 5,693,085 A | 12/1997 | Buirge et al. | |
| 5,700,286 A | 12/1997 | Tartaglia et al. | |
| 5,707,385 A | 1/1998 | Williams | |
| 5,716,981 A | 2/1998 | Hunter et al. | |
| 5,725,549 A | 3/1998 | Lam | |
| 5,726,297 A | 3/1998 | Gryaznov et al. | |
| 5,728,751 A | 3/1998 | Patnaik | |
| 5,733,925 A | 3/1998 | Kunz et al. | |
| 5,741,881 A | 4/1998 | Patnaik | |
| 5,756,457 A | 5/1998 | Wang et al. | |
| 5,756,476 A | 5/1998 | Epstein et al. | |
| 5,766,710 A | 6/1998 | Turnlund et al. | |
| 5,800,516 A | 9/1998 | Fine et al. | |
| 5,811,447 A | 9/1998 | Kunz et al. | |
| 4,739,762 B1 | 10/1998 | Palmaz | |
| 5,824,049 A | 10/1998 | Ragheb et al. | |
| 5,830,178 A | 11/1998 | Jones et al. | |
| 5,830,461 A | 11/1998 | Billiar | |
| 5,830,879 A | 11/1998 | Isner | |
| 5,833,651 A | 11/1998 | Donovan et al. | |
| 5,834,582 A | 11/1998 | Sinclair et al. | |
| 5,837,313 A | 11/1998 | Ding et al. | |
| 5,837,835 A | 11/1998 | Gryaznov et al. | |
| 5,851,508 A | 12/1998 | Greff et al. | |
| 5,854,207 A | 12/1998 | Lee et al. | |
| 5,855,618 A | 1/1999 | Patnaik et al. | |
| 5,858,746 A | 1/1999 | Hubbell et al. | |
| 5,865,814 A | 2/1999 | Tuch | |
| 5,873,904 A | 2/1999 | Ragheb et al. | |
| 5,874,165 A | 2/1999 | Drumheller | |
| 5,876,743 A | 3/1999 | Ibsen et al. | |
| 5,877,263 A | 3/1999 | Patnaik et al. | |
| 5,879,713 A | 3/1999 | Roth et al. | |
| 5,891,192 A | 4/1999 | Murayama et al. | |
| 5,897,955 A | 4/1999 | Drumheller | |
| 5,914,182 A | 6/1999 | Drumheller | |
| 5,916,870 A | 6/1999 | Lee et al. | |
| 5,942,209 A | 8/1999 | Leavitt et al. | |
| 5,948,428 A | 9/1999 | Lee et al. | |
| 5,957,975 A | 9/1999 | Lafont et al. | |
| 5,965,720 A | 10/1999 | Gryaznov et al. | |
| 5,971,954 A | 10/1999 | Conway et al. | |
| 5,980,564 A | 11/1999 | Stinson | |
| 5,980,928 A | 11/1999 | Terry | |
| 5,980,972 A | 11/1999 | Ding | |
| 5,981,568 A | 11/1999 | Kunz et al. | |
| 5,997,468 A | 12/1999 | Wolff et al. | |
| 6,015,541 A | 1/2000 | Greff et al. | |
| 6,042,875 A | 3/2000 | Ding et al. | |
| 6,048,964 A | 4/2000 | Lee et al. | |
| 6,051,648 A | 4/2000 | Rhee et al. | |
| 6,056,993 A | 5/2000 | Leidner et al. | |
| 6,060,451 A | 5/2000 | DiMaio et al. | |
| 6,071,266 A | 6/2000 | Kelley | |
| 6,074,659 A | 6/2000 | Kunz et al. | |
| 6,080,177 A | 6/2000 | Igaki et al. | |
| 6,080,488 A | 6/2000 | Hostettler et al. | |
| 6,093,463 A | 7/2000 | Thakrar | |
| 6,096,070 A | 8/2000 | Ragheb et al. | |
| 6,096,525 A | 8/2000 | Patnaik | |
| 6,099,562 A | 8/2000 | Ding et al. | |
| 6,103,230 A | 8/2000 | Billiar et al. | |
| 6,107,416 A | 8/2000 | Patnaik et al. | |
| 6,110,188 A | 8/2000 | Narciso, Jr. | |
| 6,113,629 A | 9/2000 | Ken | |
| 6,117,979 A | 9/2000 | Hendriks et al. | |
| 6,120,536 A | 9/2000 | Ding et al. | |
| 6,120,904 A | 9/2000 | Hostettler et al. | |
| 6,121,027 A | 9/2000 | Clapper et al. | |
| 6,127,173 A | 10/2000 | Eckstein et al. | |
| 6,129,761 A | 10/2000 | Hubbell | |
| 6,153,252 A | 11/2000 | Hossainy et al. | |
| 4,776,337 B1 | 12/2000 | Palmaz | |
| 6,159,951 A | 12/2000 | Karpeisky et al. | |
| 6,165,212 A | 12/2000 | Dereume et al. | |
| 6,166,130 A | 12/2000 | Rhee et al. | |
| 6,169,170 B1 | 1/2001 | Gryaznov et al. | |
| 6,171,609 B1 | 1/2001 | Kunz | |
| 6,174,330 B1 | 1/2001 | Stinson | |
| 6,177,523 B1 | 1/2001 | Reich et al. | |
| 6,224,626 B1 | 5/2001 | Steinke | |
| 6,228,845 B1 | 5/2001 | Donovan et al. | |
| 6,240,616 B1 | 6/2001 | Yan | |
| 6,245,103 B1 | 6/2001 | Stinson | |
| 6,251,135 B1 | 6/2001 | Stinson et al. | |
| 6,251,142 B1 | 6/2001 | Bernacca et al. | |
| 6,287,332 B1 | 9/2001 | Bolz et al. | |
| 4,733,665 C2 | 1/2002 | Palmaz | |
| 6,395,326 B1 | 5/2002 | Castro et al. | |
| 6,423,092 B2 | 7/2002 | Datta et al. | |
| 6,527,801 B1 | 3/2003 | Dutta | |
| 6,626,939 B1 | 9/2003 | Burnside et al. | |
| 6,656,162 B2 | 12/2003 | Santini, Jr. et al. | |
| 6,746,773 B2 | 6/2004 | Llanos et al. | |
| 6,752,826 B2 | 6/2004 | Holloway et al. | |
| 7,229,471 B2 | 6/2007 | Gale et al. | |
| 7,311,980 B1 * | 12/2007 | Hossainy et al. | 428/480 |
| 7,329,413 B1 * | 2/2008 | Pacetti et al. | 424/423 |
| 7,875,283 B2 * | 1/2011 | Hossainy et al. | 424/423 |
| 2001/0014717 A1 * | 8/2001 | Hossainy et al. | 525/60 |
| 2002/0002399 A1 | 1/2002 | Huxel et al. | |
| 2002/0004060 A1 | 1/2002 | Heublein et al. | |
| 2002/0004101 A1 | 1/2002 | Ding et al. | |
| 2002/0082679 A1 * | 6/2002 | Sirhan et al. | 623/1.15 |
| 2002/0116050 A1 | 8/2002 | Kocur | |
| 2003/0100865 A1 | 5/2003 | Santini, Jr. et al. | |
| 2003/0105518 A1 | 6/2003 | Dutta | |
| 2003/0162905 A1 | 8/2003 | Benz et al. | |
| 2004/0098095 A1 | 5/2004 | Burnside et al. | |
| 2008/0113207 A1 * | 5/2008 | Pacetti et al. | 428/483 |

(56) References Cited

U.S. PATENT DOCUMENTS

| | | | | |
|---|---|---|---|---|
| 2008/0138497 A1* | 6/2008 | Pacetti et al. | ........ | 427/2.24 |
| 2008/0138498 A1* | 6/2008 | Pacetti et al. | ........ | 427/2.24 |

FOREIGN PATENT DOCUMENTS

| | | |
|---|---|---|
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 970 711 | 1/2000 |
| EP | 1247537 A1 * | 10/2002 |
| GB | 2 247 696 | 3/1992 |
| JP | 06-41310 | 2/1994 |
| JP | 08-257055 | 10/1996 |
| JP | 2000-237298 | 9/2000 |
| JP | 2002-524207 | 8/2002 |
| JP | 2003-517890 | 6/2003 |
| JP | 2003-325655 | 11/2003 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/12243 | 3/1998 |
| WO | WO 99/08718 | 2/1999 |
| WO | WO 00/12147 | 3/2000 |
| WO | WO 00/64506 | 11/2000 |
| WO | WO 01/01890 | 1/2001 |
| WO | WO 01/54745 | 8/2001 |
| WO | WO 02/080993 | 10/2002 |
| WO | WO 03/063924 | 8/2003 |
| WO | WO 03/090807 | 11/2003 |
| WO | WO 03/094990 | 11/2003 |
| WO | WO 2004/022124 | 3/2004 |
| WO | WO 2004/023985 | 3/2004 |
| WO | WO 2005/051449 | 6/2005 |

OTHER PUBLICATIONS

Ansari, *Tubal Reanastomosis Using Absorbable Stent*, International Journal of Fertility, vol. 23, No. 1 (1978).

Ansari, *End-to-end tubal anastomosis using an absorbable stent*, Fertility and Sterility, vol. 32(2), pp. 197-201 (Aug. 1979).

Bull, *Patylene Coating for Medical Applications*, Medical Product Manufacturing News (Mar. 1993).

Casper et al., *Fiber-Reinforced Absorbable Composite for Orthopedic Surgery*, Polymeric Materials Science and Engineering, 53:497-501 (1985).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Devanathan et al., *Polymeric Conformal Coatings for Implantable Electronic Devices*, IEEE Transactions on Biomedical Engineering, vol. BME-27(11):671-675 (1980).

Feng-Chun et al., *Assessment of Tissue Blood Flow Following Small Artery Welding with an Intraluminal Dissolvable Stent*, Microsurgery, vol. 19(3), pp. 148-152 (1999).

Hahn et al., *Biocompatibility of Glow-Discharge-Polymerized Films and Vacuum-Deposited Parylene*, J Applied Polymer Sci, 38:55-64 (1984).

Hahn et al., *Glow Discharge Polymers as Coatings for Implanted Devices*, ISA, pp. 109-111 (1981).

Kelley et al., *Totally Resorbable High-Strength Composite Material*, Advances in Biomedical Polymers, 35:75-85 (1987).

Kubies et al., *Microdomain Structure in Polylactide-block-poly(ethylene oxide) Copolymer Films*, Biomaterials 21:529-536 (2000).

Kutryk et al., *Coronary Stenting: Current Perspectives*, companion to the Handbook of Coronary Stents (1999).

Muller et al., *Advances in Coronary Angioplasty: Endovascular Stents*, Coron Arter Dis, 1(4):438-448 (Jul./Aug. 1990).

Nichols et al., *Electrical Insulation of Implantable Devices by Composite Polymer Coatings*, ISA Transactions, 26(4):15-18 (1987).

Redman, *Clinical Experience with Vasovasostomy Utilizing Absorbable Intravasal Stent*, Urology, vol. 20(1), pp. 59-61 (Jul. 1982).

Rust et al., *The Effects of Absorbable Stenting on Postoperative Stenosis of the Surgically Enlarged Maxillary Sinus Ostia in a Rabbit Animal Model*, Archives of Otolaryngology, vol. 122(12), pp. 1395-1397 (Dec. 1996).

Schatz, *A View of Vascular Stents*, Circulation, 79(2):445-457 (Feb. 1989).

Schmidt et al., *Long-Term Implants of Parylene-C Coated Microelectrodes*, Med & Biol Eng & Comp, 26(1):96-101 (Jan. 1988).

Translation of Notification of Refusal for Appl. No. 2007-506274, mailed Apr. 17, 2012, 3 pgs.

Notification of Reasons for Refusal issued by JPO for Appl. No. 2007-506274, mailed Sep. 17, 2013, 3 pgs.

Translation of the Notification of Reasons for Refusal issued by JPO for Appl. No. 2007-506274, mailed Sep. 17, 2013, 6 pgs.

* cited by examiner

BIOLOGICALLY DEGRADABLE COMPOSITIONS FOR MEDICAL APPLICATIONS

RELATED APPLICATIONS

This application is a continuation of application Ser. No. 10/812,780, filed 29 Mar. 2004, which application is incorporated, including any drawings, as if fully set forth herein.

BACKGROUND

1. Field of the Invention

This invention is relates to biologically degradable compositions for medical applications such as for coatings for implantable medical devices.

2. Description of the State of the Art

A wide spectrum of devices, from vascular devices such as catheters, stents, and guidewires, to ocular devices such as intra-ocular lenses is incorporating polymeric material. Polymeric materials are being used for a variety of reasons, including making a surface of a device more biocompatible or as a vehicle for delivering a drug. Since polymeric materials are treated as a foreign object by the body's immune system, the challenge has been to make the polymers highly biocompatible as well as to reduce any fouling effects that the polymer may produce or harbor. As a better option, it may be better to make the polymer not only highly biocompatible and non-fouling, but also biodegradable such that the polymer is eliminated by the body after it has served its function. The degradation of the polymer should not create any residues that can provide adverse effects for the patient, such as excess inflammation. To the contrary, the products of degradation should enhance the treatment that is being provided to the patient or should provide medicinal effects. Should the polymeric material include a drug for local application, the composition should be capable of carrying the drug so as to release the drug at an efficacious rate for a therapeutically effective duration of time. Finally, if the material is used as a coating, the properties of the composition should be suitable so as to allow a film layer to be formed on the medical device. For devices that include body geometry that expand or fold, such as a stent or a balloon, the polymer must be flexible enough so as to expand or fold with the device without significant detachment or delamination of the coating. Tradeoffs do exist between biocompatibility, structural integrity and drug delivery capabilities of the polymer. Enhancing one characteristic may determinately affect the other. Accordingly, a proper balance must be drawn to provide for a polymeric composition that meets the specific need of the application for which it is being used.

The embodiments of the present invention provide for biocompatible polymeric compositions that can be used medical applications.

SUMMARY

A medical article is provided comprising a biologically degradable AB block copolymer and a biologically degradable polymer that is capable, at equilibrium and at room temperature, of absorbing less than about 5 mass % water. The medical article can be a stent, a graft or a stent graft. The AB block-copolymer can be capable of absorbing, at equilibrium and at room temperature, about 5 mass % or more water. The AB block-copolymer can include a biocompatible polymeric moiety and a structural polymeric moiety. The biocompatible polymeric moiety can be, for example, poly(alkylene glycol), poly(2-hydroxyethyl methacrylate), poly(3-hydroxypropyl methacrylamide), hydroxylated poly(vinyl pyrrolidone), sulfonated dextran, sulfonated polystyrene, fibrin, fibrinogen, cellulose, starch, collagen, hyaluronic acid, heparin, a graft copolymer of poly(L-lysine)-graft-co-poly(ethylene glycol), and copolymers thereof. The structural polymeric moiety can be poly(D,L-lactide), poly(caprolactone), poly(caprolactone-co-D,L-lactide), poly(butylene terephthalate), poly(ester amide), poly(aspirin), poly(L-lactide), poly(glycolide), poly(L-lactide-co-glycolide), poly(D,L-lactide-co-glycolide), poly(3-hydroxybutyrate), poly(4-hydroxybutyrate), poly(hydroxyvalerate), poly(3-hydroxybutyrate-co-valerate), poly(4-hydroxybutyrate-co-valerate), and polydioxanone. The second polymer can be poly(L-lactide), poly(D,L-lactide), poly(glycolide), poly(L-lactide-co-glycolide), poly(D,L-lactide-co-glycolide), poly(caprolactone), poly(L-lactide-co-caprolactone), poly(D,L-lactide-co-caprolactone), poly(3-hydroxybutyrate), poly(4-hydroxybutyrate), poly(hydroxyvalerate), poly(3-hydroxybutyrate-co-valerate), poly(4-hydroxybutyrate-co-valerate), poly(ester amides), poly(anhydrides), poly(carbonates), poly(trimethylene carbonate-co-glycolide), poly(trimethylene carbonate-co-L-lactide), poly(trimethylene carbonate-co-D,L-lactide), poly(dioxanone), poly(phosphazenes), poly(orthoesters), poly(tyrosine-co-carbonates), polyalkylene oxalates, poly(glycerol-co-sebacic acid esters), cyanoacrylates, poly(amino acids), poly(lysine), poly(glutamic acid) and combinations thereof.

DETAILED DESCRIPTION

Terms and Definitions

For the purposes of the present invention, the following terms and definitions apply:

The terms "biologically degradable" and "biodegradable" are used interchangeably and refer to polymers that are capable of being completely degraded and/or eroded when exposed to bodily fluids such as blood and can be gradually resorbed, absorbed and/or eliminated by the body. The processes of breaking down and eventual absorption and elimination of the polymer can be caused by, for example, hydrolysis, metabolic processes, bulk or surface erosion, and the like. For coating applications, it is understood that after the process of degradation, erosion, absorption, and/or resorption has been completed, no polymer will remain on the device. In some embodiments, very negligible traces or residue may be left behind. Whenever the terms "degradable," "biodegradable," or "biologically degradable" are used in this application, they are intended to broadly include biologically erodable, bioabsorbable, and bioresorbable polymers as well as other types of polymers that are broken down and/or eliminated by the body.

"Biodegradable polymer composition" or "biodegradable composition" is defined as a composition having a combination of at least two biologically degradable polymers. In some embodiments, the composition can also include a non-biologically degradable component or polymer. The polymers can be blended, combined, mixed, bonded, linked by linking agent, or conjugated.

The term "block-copolymer" is defined in accordance with the terminology used by the International Union for Pure and Applied Chemistry (IUPAC). "Block-copolymer" refers to a copolymer containing a linear arrangement of blocks. The block is defined as a portion of a polymer molecule in which the monomeric units have at least one constitutional or configurational feature absent from the adjacent portions. The term "AB block-copolymer" is defined as a block-copolymer having moieties A and B arranged according to the general formula

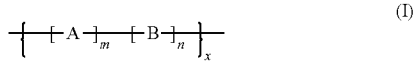

where each of "m," "n," and "x" is a positive integer, and m can be ≥2, and n can be ≥2. The blocks of the AB block-copolymers, could be, but need not be linked on the ends, since the values of the integers "m" and "n" determining the number of blocks are such as to ensure that the individual blocks are usually long enough to be considered polymers in their own right. An AB block copolymer can be, accordingly, named poly A-block-co-poly B block polymer. In some embodiments, the AB block-copolymer can be part of a chain of another polymer such as in the backbone or as a pendant or side group.

The term "moiety" is defined as a portion of a complete structure of a copolymer, the portion to include at least 2 atoms joined together in a particular way. The term "moiety" includes functional groups and/or discreet bonded residues that are present in the macromolecule of a copolymer. The term "moiety" as used in the present application is inclusive of individual units in the copolymers. The term "moiety" as used in the present application is also inclusive of entire polymeric blocks in the copolymers.

EMBODIMENTS OF THE INVENTION

The biodegradable polymer composition includes at least one biodegradable AB block-copolymer or a polymer that includes biodegradable AB blocks ("the first component") and at least one other biodegradable polymer ("the second component"). The first component can be capable of absorbing, at equilibrium and at room temperature, about 2 mass % or more water, preferably 5 mass % or more water. The second component can be capable of absorbing, at equilibrium and at room temperature, less than about 2 mass % water, preferably less than about 5 mass % water. The second component is not or does not include an AB polymeric block or can include a polymer that is substantially free of AB polymeric blocks. In other words, the second component can include a polymer the molecular structure of which is substantially free of fragments shown by formula (I) above. The ratio between the first component and the second component in the biodegradable polymer composition can be between about 1:1 and about 1:99, more narrowly, between about 1:2 and about 1:49, for example, about 1:19.

The First Component (AB Block-Copolymer)

The AB block copolymer can be capable of absorbing, at equilibrium and at room temperature, about 2 mass %, preferably about 5 mass % or more water. AB block copolymers that can be used comprise two polymeric moieties A and B. The first polymeric moiety is a biocompatible moiety that can be capable of providing the block-copolymer with blood compatibility. The second polymeric moiety is a structural moiety that can be capable of providing the block-copolymer with mechanical and/or adhesive properties. The structural moiety allows the copolymer to form a film layer on substrates, such as metallic stents. Moiety A can be the biocompatible moiety and moiety B can be the structural moiety. In some embodiments, Moiety B can be the biocompatible moiety and moiety A can be the structural moiety. The mass ratio between be the biocompatible moiety and the structural moiety can be between about 1:9 and about 1:0.7, for example, about 1:0.81. The mass ratio 1:0.81 corresponds to an AB block-copolymer comprising about 55 mass % the biocompatible moiety and the balance, the structural moiety.

The biocompatible and the structural moieties can be selected to make the AB block-copolymers biologically degradable. Molecular weight of a biocompatible moiety that can be used can be below 40,000 Daltons, for example, between about 300 and 20,000 Daltons. To illustrate, one example of a biocompatible moiety A that can be used is poly(ethylene glycol) (PEG) having the molecular weight between about 300 and 20,000 Daltons. In this example (when the A moiety is PEG), the value of "m" in formula (I) can be between about 5 and about 1,000.

In addition to PEG, other poly(alkylene glycols) can be used to form the biocompatible moiety, for example, poly (propylene glycol) (PPG), poly(tetramethylene glycol), or poly(ethylene oxide-co-propylene oxide). Examples of other biocompatible moieties that can be used include poly(2-hydroxyethyl methacrylate), poly(3-hydroxypropyl methacrylamide), hydroxylated poly(vinyl pyrrolidone), sulfonated dextran, sulfonated polystyrene, fibrin, fibrinogen, cellulose, starch, collagen, hyaluronic acid, heparin, poly(L-lysine)-graft-co-poly(ethylene glycol), which is a graft copolymer of poly(L-lysine) and PEG, or copolymers thereof.

Molecular weight of a structural moiety that can be used can be between about 20,000 and about 200,000 Daltons, more narrowly, between about 40,000 and about 100,000 Daltons, for example, about 60,000 Daltons. To illustrate, one example of a structural moiety B that can be used is poly(D, L-lactide) having the molecular weight between about 20,000 and about 200,000 Daltons. In this example, the value of "n" in formula (I) can be between about 250 and about 3,000.

In addition to poly(D,L-lactide), other structural moieties can be used. Some examples of such moieties include poly (caprolactone) (PCL), poly(caprolactone-co-D,L-lactide), poly(butylene terephthalate) (PBT), poly(ester amide), poly (aspirin), poly(L-lactide), poly(glycolide), poly(L-lactide-co-glycolide), poly(D,L-lactide-co-glycolide), poly(3-hydroxybutyrate), poly(4-hydroxybutyrate), poly (hydroxyvalerate), poly(3-hydroxybutyrate-co-valerate), poly(4-hydroxybutyrate-co-valerate), and polydioxanone.

One example of the biodegradable AB block copolymer is poly(ethylene-glycol)-block-co-poly(caprolactone) (PEG-PCL). One possible structure of the PEG-PCL block copolymer can be illustrated by formula (II):

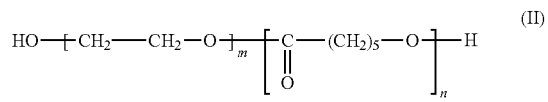

wherein m are n are positive integers.

In PEG-PCL block copolymer shown by formula (II), the PEG blocks constitute the biocompatible moiety A, while the PCL block constitutes the structural moiety B. Block copolymer shown by formula (II) can be synthesized by standard methods known to those having ordinary skill in the art, for example, copolycondensation of PEG with PCL. The process of copolycondensation can be catalyzed by a catalyst which can be selected by those having ordinary skill in the art, for example, by an acid catalyst or a base catalyst.

Another example of the PEG-containing polyester includes a block-copolymer of PEG with PBT, such as the block copolymer shown by formula (III):

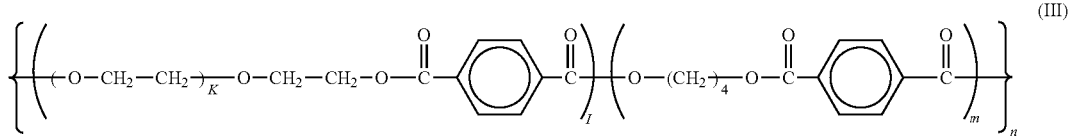

wherein m, n, I and K are positive integers.

The PEG-PBT block-copolymer can be obtained by a synthetic process that can be selected by those having ordinary skill in the art. One example of the synthetic process that can be used includes trans-esterification of dibutyleneterephthalate with PEG. One brand of PEG-PBT block copolymer is known under a trade name PolyActive™ and is available from IsoTis Corp. of Holland. In PEG-PBT, the ratio between the PEG units and the PBT units can be between about 0.67:1 and about 9:1. The molecular weight of the PEG units can be between about 300 and about 4,000 Daltons.

PEG-PCL and PEG-PBT block copolymers all contain fragments with ester bonds. Ester bonds are known to be water-labile bonds. When in contact with slightly alkaline blood, ester bonds are subject to catalyzed hydrolysis, thus ensuring biological degradability of the block-copolymer. One product of degradation of every block polymer, belonging to the group PEG-PCL and PEG-PBT, is expected to be PEG, which is highly biologically compatible. PEG also has an additional advantage of being biologically active, reducing smooth muscle cells proliferation at the lesion site and thus capable of treating, delaying, preventing or inhibiting restenosis.

The Second Component

The second component of the composition can comprise at least one biodegradable polymer capable of absorbing, at equilibrium and at room temperature, less than about 2 mass %, preferably less than 5 mass % water.

Examples of suitable biodegradable polymers that can be used as a second component of the biodegradable polymer composition include poly(L-lactide), poly(D,L-lactide), poly(glycolide), poly(L-lactide-co-glycolide), poly(D,L-lactide-co-glycolide), poly(caprolactone), poly(L-lactide-co-caprolactone), poly(D,L-lactide-co-caprolactone), polyhydroxyalkanoates, poly(3-hydroxybutyrate), poly(4-hydroxybutyrate), poly(hydroxyvalerate), poly(3-hydroxybutyrate-co-valerate), poly(4-hydroxybutyrate-co-valerate), poly(ester amides), poly(anhydrides), poly(carbonates), poly(trimethylene carbonate-co-glycolide), poly(trimethylene carbonate-co-L-lactide), poly(trimethylene carbonate-co-D,L-lactide), poly(dioxanone), poly(phosphazenes), poly(orthoesters), poly(tyrosine-co-carbonates), polyalkylene oxalates, poly(glycerol-co-sebacic acid esters), cyanoacrylates, poly(amino acids), poly(lysine), poly(glutamic acid) and mixtures thereof.

Optional Third Components

In some embodiments, a third component can be included, mixed, blended, bonded, conjugated or linked with the composition. This can be a drug, an active agent, or a therapeutic substance. In some embodiments, another polymer can be included, mixed, blended, bonded, conjugated or linked with the composition. These polymers need not be biodegradable. Examples include polyacrylates, such as poly(butyl methacrylate), poly(ethyl methacrylate), and poly(ethyl methacrylate-co-butyl methacrylate), and fluorinated polymers and/or copolymers, such as poly(vinylidene fluoride) and poly(vinylidene fluoride-co-hexafluoro propene), poly(vinyl pyrrolidone), polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins, e.g., poly(ethylene-co-vinyl alcohol) (EVAL), ethylene-methyl methacrylate copolymers, acrylonitrile-styrene copolymers, ABS resins, and ethylene-vinyl acetate copolymers, polyamides (such as Nylon 66 and polycaprolactam), alkyd resins, polyoxymethylenes, polyimides, polyethers, epoxy resins, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

The therapeutic substance can include any substance capable of exerting a therapeutic, diagnostic or prophylactic effect for a patient. The therapeutic substance may include small molecule substances, peptides, proteins, oligonucleotides, and the like. The therapeutic substance could be designed, for example, to inhibit the activity of vascular smooth muscle cells. It can be directed at inhibiting abnormal or inappropriate migration and/or proliferation of smooth muscle cells to inhibit restenosis.

Examples of therapeutic substances include antiproliferative substances such as actinomycin D, or derivatives and analogs thereof (manufactured by Sigma-Aldrich of Milwaukee, Wis., or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as ANGIOMAX (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of EVEROLIMUS available from Novartis), 40-O-(3-hydroxy)propyl-rapamycin, 40-O—[2-(2-hydroxy)ethoxy]ethyl-rapamycin, and 40-O-tetrazole-rapamycin, prodrugs thereof, co-drugs thereof, and combinations thereof.

Application of the Composition

The composition can have a variety of medical applications, such as coatings for medical devices, coatings for implantable prostheses, capsules for drugs, drug delivery particles as well as devices made at least in part from the composition. Examples of medical devices, that can be used in conjunction with the embodiments of this invention include stents (e.g., self expandable or balloon expandable), biodegradable stents, stent-grafts, grafts (e.g., aortic grafts), catheters, balloons, coating on balloons, guidewires, artificial hearts and valves, blood oxygenerators, ventricular assist devices, cardiopulmonary bypass systems, cerebrospinal fluid shunts, pacemaker electrodes, axius coronary shunts and leads as well as other devices such as intraocular lenses. The devices, e.g., the stent, can be made from a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used or coated with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Drug Delivery Stent

A coating for a stent made from the composition of the present invention can be a multi-layer structure and can include a primer layer; a drug-polymer layer (also referred to as "reservoir" or "reservoir layer") or alternatively a polymer free drug layer; and/or a topcoat layer. Intermediary layers can also be provided. Each layer of the stent coating can be formed on the stent by dissolving the biodegradable polymer composition in a solvent, or a mixture of solvents, and applying the resulting solution on the stent by spraying or immersing the stent in the solution. At least one of the layers should include the biodegradable polymeric composition of the present invention. The remaining portion of a layer or the other layers can be made from other polymeric material, such as poly(butyl methacrylate), poly(ethyl methacrylate), and poly(ethyl methacrylate-co-butyl methacrylate), or the others disclosed above.

Preferably, the outer most layer (e.g., the reservoir layer or the topcoat layer) is made from the biodegradable composition. If a topcoat layer is used, the topcoat layer can be made from the biodegradable polymer. The reservoir layer or the optional primer layer can be made from the same composition, the same composition but with different ratios of the first to second component, the same composition but with different ratios of the first to second to third component or from a different polymeric material.

In some embodiments at least two of the layers can be made from the embodiments of the biodegradable polymeric composition such that for each layer the ratio of the first to second component is different. In some embodiments, if a third component is used, the ratio of the first to second to third component can be different for each layer.

After the solution has been applied onto the stent, the coating is dried by allowing the solvent to evaporate. The process of drying can be accelerated if the drying is conducted at an elevated temperature.

Representative examples of some solvents suitable for making the coating solution include N,N-dimethylacetamide (DMAC), N,N-dimethylformamide (DMF), tetrahydrofurane (THF), cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used as well. Representative examples of the mixtures include DMAC and methanol (e.g., a 50:50 by mass mixture); water, i-propanol, and DMAC (e.g., a 10:3:87 by mass mixture); i-propanol and DMAC (e.g., 80:20, 50:50, or 20:80 by mass mixtures); acetone and cyclohexanone (e.g., 80:20, 50:50, or 20:80 by mass mixtures); acetone and xylene (e.g. a 50:50 by mass mixture); acetone, FLUX REMOVER AMS, and xylene (e.g., a 10:50:40 by mass mixture); and 1,1,2-trichloroethane and chloroform (e.g., a 80:20 by mass mixture). FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer being dissolved.

To incorporate a drug into the reservoir layer, the drug in a form of a solution can be combined with the polymer solution that is applied onto the stent as described above. Alternatively, to fabricate a polymer free drug layer, the drug can be dissolved in a suitable solvent or mixture of solvents, and the resulting drug solution can be applied on the stent by spraying or immersing the stent in the drug solution. Instead of introducing the drug in a solution, the drug can be introduced as a colloid system, such as a suspension in an appropriate solvent phase. To make the suspension, the drug can be dispersed in the solvent phase using conventional techniques used in colloid or emulsion chemistry. Depending on a variety of factors, e.g., the nature of the drug, those having ordinary skill in the art can select the suitable solvent to form the solvent phase of the suspension, as well as the quantity of the drug to be dispersed in the solvent phase. The suspension can be mixed with a polymer solution and the mixture can be applied on the stent as described above. Alternatively, the drug suspension can be applied on the stent without being mixed with the polymer solution.

The biological degradation of the biodegradable polymer composition is expected to cause an increase of the rate of release of the drug due to the gradual disappearance of the polymer that forms the reservoir and/or the topcoat layer. By choosing an appropriate biodegradable polymer composition or by varying the ratio of the components of the composition, or by including a third polymeric component to the matrix, a stent coating having a costumed release rate can be engineered.

Method of Use

In accordance with embodiments of the invention, a coating of the various described embodiments can be formed on an implantable device or prosthesis, e.g., a stent. For coatings including one or more active agents, the agent will be retain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

The compositions of the invention can be used for the treatment of a variety of disorder in mammals including atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, cancer as well as other disorders.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The following examples are provided to further illustrate embodiments of the present invention.

Example 1

A first composition can be prepared by mixing about 1.0 mass % to about 15 mass %, for example, about 2.0 mass % poly(caprolactone) (PCL); and the balance, mixture of tetrahydrofuran (THF) and xylene solvents, where a mass ratio between THF and xylene was about 3:1. The first composition can be applied onto the surface of a bare 12 mm VISION stent (available from Guidant Corporation) by spraying and dried to form a primer layer. A spray coater was used, having a 0.014 fan nozzle maintained at about 60° C. with a feed pressure of about 0.2 atm (about 3 psi) and an atomization pressure of about 1.3 atm (about 20 psi). About 75 μg of the wet coating can be applied. The primer was baked at about 60° C. for about 2 hours, yielding a dry primer layer.

A second composition can be prepared by mixing about 1.0 mass % to about 15 mass %, for example, about 2.0 mass % PCL; about 0.05 mass % to about 2.0 mass %, for example, about 1.0 mass % EVEROLIMUS; and the balance, THF/xylene solvent mixture described above. The second composition can contain about 300 μg PCL and about 150 μg EVEROLIMUS. The second composition can be applied onto the dried primer layer to form the reservoir layer, using the same spraying technique and equipment used for applying the primer layer, followed by drying, e.g., by baking at about 50° C. for about 1 hour. A third composition can prepared by mixing about 1.0 mass % to about 15 mass %, for example, about 2.0 mass % PCL; about 1.0 mass % to about 15 mass %, for example, about 2.0 mass % PEG-PBT (4000PEGT80PBT20); and the balance, THF/xylene solvent mixture described above.

The brand of PEG-PBT that can be used can have about 20 molar % PBT units and about 80 molar % PEG units. The molecular weight of the PEG units was about 4,000 Daltons. The third composition can contain about 50 μg PCL and about 50 μg PEG-PBT. The third composition can be applied onto the dried reservoir layer to form a topcoat layer, using the same spraying technique and equipment used for applying the primer layer and the reservoir layer, followed by drying at about 50° C. for about 1 hour.

Example 2

A primer and reservoir layers can be formed on a stent as described in Example 1. A composition can be prepared by mixing about 1.0 mass % to about 15 mass %, for example, about 2.0 mass % poly(L-lactide); about 1.0 mass % to about 15 mass %, for example, about 2.0 mass % PEG-PBT; and the balance, the mixture of chloroform and tricholoethane solvents, wherein the mass ratio between chloroform and trichlorethane can be about 1:1. The same brand of PEG-PBT as described in Example 1 can be used. The composition can contain about 60 μg poly(L-lactide), about 40 μg PEG-PBT, and if desired, about 200 μg paclitaxel. The composition can be applied onto the dried reservoir layer to form a topcoat layer.

Example 3

A primer and reservoir layers can be formed on a stent as described in Example 1, except rapamycin can be used instead of EVEROLIMUS. A composition can be prepared by mixing about 1.0 mass % to about 15 mass %, for example, about 1.5 mass % poly(ester amide); about 1.0 mass % to about 15 mass %, for example, about 0.5 mass % PEG-PBT; and the balance, a mixture of ethanol and DMAC solvents, wherein mass ratio between ethanol and DMAC can be about 1:1.

The same brand of PEG-PBT as described in Example 1 can be used. Poly(ester amide)-8,4 having the formula (IV) can be used:

$$\left[ \begin{array}{c} \overset{\text{C}}{\underset{\text{O}}{\|}} - (CH_2)_8 - \overset{\text{C}}{\underset{\text{O}}{\|}} - O - CH_2 - \overset{\text{C}}{\underset{\text{O}}{\|}} - NH - (CH_2)_4 - NH - \overset{\text{C}}{\underset{\text{O}}{\|}} - CH_2 - O \end{array} \right]_n \quad \text{(IV)}$$

wherein n is a positive integer.

The composition can contain about 75 μg poly(ester amide), and about 25 μg PEG-PBT. The composition can be applied onto the dried reservoir layer to form a topcoat layer, using the same spraying technique and equipment as described above, followed by drying, e.g., by baking. The poly(ester amide) shown by formula (IV) is expected to degrade when exposed to bodily fluids such as blood to yield sebacic and glycolic acids and 1,4-butanediamine (putrescine), all of which are biocompatible.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article comprising:
   (a) a medical substrate; and
   (b) a coating deposited on the substrate, the coating comprising a first polymer and a second polymer, wherein the first polymer is a biologically degradable AB block copolymer, and the second polymer is a biologically degradable polymer that is capable of absorbing, as determined at equilibrium and at room temperature, less than 5% water by mass of the biologically degradable polymer,
   wherein the AB block-copolymer is of the formula:

$$\left\{ \left[ \left( O-CH_2-CH_2 \right)_K O-CH_2-CH_2-O-\overset{O}{\underset{\|}{C}}-\bigcirc- \right. \right.$$
$$\left. \left. -\overset{O}{\underset{\|}{C}} \right] \left[ O-(CH_2)_4-O-\overset{O}{\underset{\|}{C}}-\bigcirc-\overset{O}{\underset{\|}{C}} \right]_m \right\}_n$$

wherein m, n, I, and K are positive integers;
   wherein the AB block-copolymer is capable of absorbing, as determined at equilibrium and at room temperature, about 5% or more water by mass of the AB block-copolymer; and
   wherein the second polymer is poly(L-lactide);
   wherein the ratio between the first polymer and the second polymer is between about 1:2 and about 1:49.

2. The medical article of claim 1, wherein the ratio between the first polymer and the second polymer is 1:19.

3. The medical article of claim 1, wherein the medical article is a stent, graft, or a stent-graft.

4. The medical article of claim 1, wherein the second polymer does not include or is substantially free from AB polymeric blocks.

5. The medical article of claim 1, additionally comprising a therapeutic substance.

6. The medical article of claim 1, wherein at least one coating layer in the coating on the substrate comprises both the first polymer and the second polymer.

7. The medical article of claim 6, wherein the at least one coating layer comprising both the first and the second polymers is the outermost layer.

8. The medical article of claim 7, wherein the outermost layer is a reservoir layer.

9. The medical article of claim 7, wherein the outermost layer is a topcoat layer.

10. The medical article of claim 6, wherein the coating further comprises at least one member of the group consisting of poly(butyl methacrylate), poly(ethyl methacrylate), and poly(ethyl methacrylate-co-butyl methacrylate).

11. The medical article of claim 10, wherein the at least one layer comprising the first and the second polymer comprises the at least one member of the group consisting of poly(butyl methacrylate), poly(ethyl methacrylate), and poly(ethyl methacrylate-co-butyl methacrylate).

12. The medical article of claim 10, wherein a layer other than the at least one layer comprising the first and the second polymer comprises the at least one member of the group consisting of poly(butyl methacrylate), poly(ethyl methacrylate), and poly(ethyl methacrylate-co-butyl methacrylate).

13. The medical article of claim 5, wherein the therapeutic substance is selected from the group consisting of tacrolimus, dexamethasone, rapamycin, 40-0-(2-hydroxy)ethyl-rapamycin (everolimus), 40-0-(3-hydroxy)propyl-rapamycin, 40-0-[2-(2-hydroxy)ethoxy]ethyl-rapamycin, and 40-0-tetrazole-rapamycin, and combinations thereof.

14. The medical article of claim 5, wherein the therapeutic substance is rapamycin, everolimus, 40-0-tetrazole-rapamycin, or a combination thereof.

15. The medical article of claim 5, wherein the therapeutic substance is selected from the group consisting of paclitaxel, docetaxel, methotrexate, azathioprine, vincristine, vinblastine, fluorouracil, doxorubicin Hydrochloride, mitomycin, and combinations thereof.

16. The medical article of claim 1, wherein in the AB block-copolymer the ratio of PEG units and the PBT units is between about 0.67:1 and about 9:1 and the molecular weight of the PEG units is between about 300 and about 4000 Daltons.

17. A method of treating a disorder in a human being, comprising:
   implanting in the human being the medical article as defined in claim 1, wherein the disorder is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and combinations thereof.

* * * * *